(12) United States Patent
Bambrilla et al.

(10) Patent No.: US 11,654,255 B2
(45) Date of Patent: *May 23, 2023

(54) JET PUMP ADAPTOR FOR VENTILATION SYSTEM

(71) Applicant: BREATHE TECHNOLOGIES, INC., Irvine, CA (US)

(72) Inventors: Enrico Bambrilla, Irvine, CA (US); Samir S. Ahmad, San Diego, CA (US)

(73) Assignee: BREATHE TECHNOLOGIES, INC., Irvine, CA (US)

( * ) Notice: Subject to any disclaimer, the term of this patent is extended or adjusted under 35 U.S.C. 154(b) by 1024 days.

This patent is subject to a terminal disclaimer.

(21) Appl. No.: 16/430,202

(22) Filed: Jun. 3, 2019

(65) Prior Publication Data

US 2019/0282773 A1 Sep. 19, 2019

Related U.S. Application Data

(63) Continuation of application No. 14/020,032, filed on Sep. 6, 2013, now Pat. No. 10,307,552.

(51) Int. Cl.
*A61M 16/00* (2006.01)
*A61M 16/08* (2006.01)
(Continued)

(52) U.S. Cl.
CPC ........ *A61M 16/0096* (2013.01); *A61M 16/06* (2013.01); *A61M 16/0858* (2014.02);
(Continued)

(58) Field of Classification Search
CPC .............. A61M 16/0096; A61M 16/06; A61M 16/0858; A61M 16/125; A61M 16/206;
(Continued)

(56) References Cited

U.S. PATENT DOCUMENTS

| | | | |
|---|---|---|---|
| 3,714,944 A | 2/1973 | Price et al. | |
| 3,726,274 A | 4/1973 | Bird et al. | |

(Continued)

FOREIGN PATENT DOCUMENTS

| | | | |
|---|---|---|---|
| CN | 102438684 A | 5/2012 | |
| CN | 103140253 A | 6/2013 | |

(Continued)

OTHER PUBLICATIONS

International Search Report and Written Opinion for PCT/US2014/052185 (10 pages), dated Dec. 17, 2014.

(Continued)

*Primary Examiner* — Victoria Murphy
(74) *Attorney, Agent, or Firm* — Stetina Brunda Garred and Brucker; Mark B. Garred

(57) ABSTRACT

In accordance with the present invention, there is provided an adaptor or attachment which is suitable for integration into the patient circuit of a ventilation system, such as a non-invasive open ventilation system, is configured for attachment to any standard ventilation mask, and is outfitted with a jet pump which creates pressure and flow by facilitating the entrainment of ambient air. The adaptor comprises a base element and a nozzle element which are operatively coupled to each other. The base element further defines a throat and at least one entrainment port facilitating a path of fluid communication between the throat and ambient air. The nozzle element includes a jet nozzle, and a connector which is adapted to facilitate the fluid coupling of the nozzle element to a bi-lumen tube of the patient circuit. The connector includes both a delivery port and a sensing port. The jet nozzle and the delivery port collectively define a delivery line or lumen which fluidly communicates with the throat of the base element, and is placeable into fluid (Continued)

communication with the delivery lumen of the bi-lumen tube.

20 Claims, 6 Drawing Sheets

(51) Int. Cl.
    *A61M 16/20*     (2006.01)
    *A61M 16/06*     (2006.01)
    *A61M 16/12*     (2006.01)
    *A61M 16/10*     (2006.01)

(52) U.S. Cl.
    CPC ........ *A61M 16/125* (2014.02); *A61M 16/206* (2014.02); *A61M 16/208* (2013.01); *A61M 16/0057* (2013.01); *A61M 16/0875* (2013.01); *A61M 16/106* (2014.02); *A61M 16/1045* (2013.01); *A61M 16/1055* (2013.01); *A61M 16/127* (2014.02); *A61M 2016/0027* (2013.01); *A61M 2205/584* (2013.01); *A61M 2205/6081* (2013.01)

(58) Field of Classification Search
    CPC ............ A61M 16/208; A61M 16/0057; A61M 16/0875; A61M 16/1045; A61M 16/1055; A61M 16/106; A61M 16/127; A61M 2016/0027; A61M 2205/584; A61M 2205/6081; A61M 11/06; B05F 3/02; F17C 5/06; F17C 13/045; B01F 3/02; B01F 3/04
    See application file for complete search history.

(56) References Cited

U.S. PATENT DOCUMENTS

| | | | |
|---|---|---|---|
| 3,850,171 A | 11/1974 | Ball et al. | |
| 3,859,995 A | 1/1975 | Colston | |
| 3,913,607 A | 10/1975 | Price | |
| 4,417,573 A | 11/1983 | De Vries | |
| 4,417,972 A | 11/1983 | Francis et al. | |
| 4,584,998 A * | 4/1986 | McGrail | A61M 16/0484 128/207.15 |
| 4,612,929 A | 9/1986 | Schuebert et al. | |
| 4,796,617 A * | 1/1989 | Matthews | A61M 16/0465 128/207.15 |
| 5,036,847 A | 8/1991 | Boussignac et al. | |
| 5,697,361 A * | 12/1997 | Smith | A62B 7/12 128/204.15 |
| 6,014,972 A | 1/2000 | Sladek | |
| 7,278,423 B2 * | 10/2007 | Serowski | A61M 16/0825 128/205.24 |
| 10,307,552 B2 * | 6/2019 | Bambrilla | A61M 16/0096 |
| 2008/0105257 A1 * | 5/2008 | Klasek | A61M 16/0633 128/203.26 |
| 2010/0071693 A1 * | 3/2010 | Allum | A61M 16/0833 128/205.24 |
| 2010/0252040 A1 | 10/2010 | Kapust et al. | |
| 2012/0085348 A1 | 4/2012 | Chalvignac et al. | |
| 2012/0204872 A1 | 8/2012 | Cohen | |
| 2013/0190643 A1 | 7/2013 | Brambilla | |

FOREIGN PATENT DOCUMENTS

| | | |
|---|---|---|
| EP | 245142 B1 | 3/1991 |
| WO | 2011029074 A1 | 3/2011 |
| WO | 2012106373 A2 | 8/2012 |

OTHER PUBLICATIONS

Chinese Office Action for CN201480049240.9, dated Dec. 2, 2016.
Chinese Office Action for CN201480049240.9, dated Nov. 9, 2017.
European Search Report for EP 14 841 576.3; dated Mar. 30, 2017.

* cited by examiner

JET PUMP ADAPTOR FOR VENTILATION SYSTEM

CROSS-REFERENCE TO RELATED APPLICATIONS

This application is a continuation of U.S. patent application Ser. No. 14/020,032, filed Sep. 6, 2013 and entitled "JET PUMP ADAPTOR FOR VENTILATION SYSTEM," the entire disclosure of which is wholly incorporated by reference herein.

STATEMENT RE: FEDERALLY SPONSORED RESEARCH/DEVELOPMENT

Not Applicable

BACKGROUND OF THE INVENTION

1. Field of the Invention

The present invention relates to systems and methods for controlling delivery of a pressurized flow of breathable gas to a patient and, more particularly, to an adaptor or attachment which is suitable for integration into the patient circuit of a ventilation system, such as a non-invasive open ventilation system, is configured for attachment to any standard ventilation mask, and is outfitted with a jet pump to facilitate the entrainment of ambient air.

2. Description of the Related Art

As is known in the medical arts, mechanical ventilators comprise medical devices that either perform or supplement breathing for patients. The vast majority of contemporary ventilators use positive pressure to deliver gas to the patient's lungs via a patient circuit between the ventilator and the patient. The patient circuit typically consists of one or two large bore tubes (e.g., from 22 mm ID for adults to 8 mm ID for neonatal) that interface to the ventilator on one end, and a patient mask on the other end. Most often, the patient mask is not provided as part of the ventilation system, and a wide variety of patient masks can be used with any ventilator.

Current ventilators are designed to support either "vented" or "leak" circuits, or "non-vented" or "non-leak" circuits. In vented circuits, the mask or patient interface is provided with an intentional leak, usually in the form of a plurality of vent openings. Ventilators using this configuration are most typically used for less acute clinical requirements, such as the treatment of obstructive sleep apnea or respiratory insufficiency. In non-vented circuits, the patient interface is usually not provided with vent openings. Non-vented circuits can have single limb or dual limb patient circuits, and an exhalation valve. Ventilators using non-vented patient circuits are most typically used for critical care applications.

Vented patient circuits are used only to carry gas flow from the ventilator to the patient and patient mask, and require a patient mask with vent openings. When utilizing vented circuits, the patient inspires fresh gas from the patient circuit, and expires $CO_2$-enriched gas, which is typically purged from the system through the vent openings in the mask. When utilizing non-vented dual limb circuits, the patient inspires fresh gas from one limb (the "inspiratory limb") of the patient circuit and expires $CO_2$-enriched gas from the second limb (the "expiratory limb") of the patient circuit. Both limbs of the dual limb patient circuit are connected together in a "Y" proximal to the patient to allow a single connection to the patient mask. When utilizing non-vented single limb circuits, an expiratory valve is placed along the circuit, usually proximal to the patient. During the inhalation phase, the exhalation valve is closed to the ambient and the patient inspires fresh gas from the single limb of the patient circuit. During the exhalation phase, the patient expires $CO_2$-enriched gas from the exhalation valve that is open to ambient.

In the patient circuits described above, the ventilator pressurizes the gas to be delivered to the patient inside the ventilator to the intended patient pressure, and then delivers that pressure to the patient through the patient circuit. Very small pressure drops develop through the patient circuit, typically around 1 $cmH_2O$, due to gas flow though the small amount of resistance created by the tubing. Some ventilators compensate for this small pressure drop either by mathematical algorithms, or by sensing the tubing pressure more proximal to the patient.

In the prior art, ventilation systems are know which integrate either a venturi or a jet pump. Generally speaking, a venturi functions to speed up a fluid in a tube using a restrictor to create negative pressure. In contrast, a jet pump uses a high speed jet in ambient air to facilitate the entrainment of ambient air. Along these lines, the prior art includes ventilation systems which incorporate entrainment masks and are used for the purpose of delivering air in combination with another therapeutic gas (e.g., oxygen) to a patient. For example, high flow oxygen delivery systems exist that include an air entrainment mask which, in addition to being designed to fit over the patient's nose and mouth and to connect to oxygen supply tubing, comprises a jet orifice and air entrainment ports. Oxygen under pressure is forced through a small jet orifice entering the mask. The velocity increase causes a shearing effect distal to the jet orifice, which in turn causes room air to be entrained into the mask via the ports formed therein. These oxygen therapy entrainment systems are used to, among other things, deliver proper mixtures of air and oxygen.

However, the prior art is generally lacking in providing non-invasive open ventilation systems wherein a jet pump, as opposed to a venturi, is integrated into the tubing of a patient circuit, rather than into the patient interface or mask of the patient circuit. The present invention, as will be described in more detail below, addresses this deficiency in the prior art.

SUMMARY OF THE INVENTION

In accordance with the present invention, there is provided an adaptor or attachment which is suitable for integration into the patient circuit of a ventilation system, such as a non-invasive open ventilation system, is configured for attachment to any standard ventilation mask, and is outfitted with a jet pump which creates pressure and flow by facilitating the entrainment of ambient air. The preferred patient interface used in conjunction with the adaptor of the present invention is a non-vented (or non-leak) nasal mask or full face mask (FFM). However, the adaptor may also be used in conjunction to a traditional vented nasal mask or full face mask, such as those used for continuous positive airway pressure (CPAP), bi-level PAP or bi-level therapy.

In accordance with a first embodiment of the present invention, the adaptor comprises a base element and a nozzle element which are operatively coupled to each other. More particularly, the nozzle element may be rotatably connected to the base element as allows for the rotation of the nozzle element relative to the base element. The base element defines a standard 22 mm ISO taper connector which allows for the releasable attachment of the adaptor to any standard ventilation mask. The base element further defines a throat and at least one entrainment port facilitating a path of fluid communication between the throat and ambient air.

The nozzle element includes a jet nozzle, and a connector which is adapted to facilitate the fluid coupling of the nozzle element to a bi-lumen tube of the patient circuit, such bi-lumen tube defining both a gas delivery lumen and a sensing lumen which is fluidly isolated from the gas delivery lumen. The connector includes both a delivery port and a sensing port. The jet nozzle and the delivery port collectively define a gas delivery line or lumen which fluidly communicates with the throat of the base element, and is placeable into fluid communication with the delivery lumen of the bi-lumen tube. In addition, the nozzle and base elements, when attached to other, collectively define a pressure sensing line or lumen which is fluidly isolated from both the delivery lumen and the throat, and is placeable into fluid communication with the sensing lumen of the bi-lumen tube. In this regard, a portion of the sensing lumen is defined by the base element (including the sensing port thereof), with another portion of the sensing lumen being defined by the nozzle element. These separate portions of the sensing lumen are brought in fluid communication with each other when the nozzle element is connected to the base element. The jet nozzle, in combination with the throat and the entrainment port, creates a jet pump within the adaptor. It is contemplated that the nozzle element can be molded with different jet nozzle sizes in order to change the performances of the jet pump (e.g., more or less pressure or flow) and can further be color coded so that the user can easily understand the jet pump performance provided thereby.

In the patient circuit outfitted with the adaptor, the jet pump in the patient circuit is able to generate a maximum pressure of about 30 cm H2O (and preferably about 20 cm H2O), and a peak flow of about 100 l/min (and preferably 60 l/min). Pressure and flow are generated in a manner wherein the breathable gas (O2, air, or other mixtures of breathable gas) is delivered to the jet nozzle of the jet pump and ambient air is entrained through the entrainment port. The flow of pressurized air is delivered to the patient through the standard ISO taper connection with the non-vented mask. The pressure sensing line of the adaptor is used to sense the pressure in the mask or to trigger a breath when breath-by-breath ventilation is provided by the ventilation system. In the first embodiment, the gas exhaled by the patient may be exhausted through the entrainment port. It is further contemplated that an HME and/or antibacterial filter can be connected between the jet pump and the connector of the mask.

In accordance with a second embodiment of the present invention, the jet pump of the adaptor may be equipped with an anti-asphyxia valve (AAV) in order to reduce the back pressure during exhalation. More particularly, an exhalation valve or AAV may be used to decrease expiratory pressure in the case when the throat of the jet pump is too small or in case of failure of the ventilator or gas source. The valve may incorporate a conical diaphragm valve that is stretched to seal against one or more exhalation ports of the adaptor (which are separate from the entrainment port) when there is positive pressure and flow in the jet pump, and opens in a manner unblocking the exhalation ports when the jet pump is not activated (i.e. during exhalation). The same function can be achieved thorough the use of a flapper valve as an alternative to the aforementioned diaphragm.

In accordance with a third embodiment of the present invention, the jet pump of the adaptor may be equipped with a exhalation/positive end expiratory pressure (PEEP) valve (or a connection for a third party PEEP valve). More particularly, the jet pump may incorporate a piloted exhalation valve. The valve can be piloted between on/off states or could be piloted in a proportional fashion to achieve positive end expiratory pressure (PEEP) control by using the pressure in the delivery line that feeds the jet nozzle via a pilot line. In this way, the valve opens and closes in sync with the breathing pattern of the patient. During inhalation, when the jet flow is delivered to the jet pump, the valve is closed by the high pressure in the nozzle delivery lumen. During exhalation there is either no flow delivered by the jet nozzle (and hence no pressure in the delivery lumen) and the valve opens, or a small flow and pressure can be maintained in the delivery lumen so that the jet pump can create back pressure in the throat against exhalation and the valve can be servoed with positive pressure to vary the resistance. This latter system results in a controllable PEEP value and requires a careful sizing and matching of the jet pump performances at low flow and the PEEP valve characteristic. This is made easier using a closed loop control over the pressure sensed by the sensing lumen of the patient circuit. The valve can also be used as a PEEP valve by using a spring to maintain PEEP and the pilot line to close during inhalation. In this embodiment the PEEP value can be adjusted by changing the pre-load of the spring (e.g., by rotating a portion of the housing). Optionally, for a better PEEP control, a non-return valve (e.g. an umbrella valve) can be used to close the throat of the jet pump during exhalation.

In accordance with a fourth embodiment of the present invention, the jet pump of the adaptor may employ a fixed PEEP valve in the shape of, for example, a flapper valve at the end of the throat. The valve is normally close (i.e., rests against the throat of the jet pump) and opens during inhalation when positive pressure and flow are established by the jet flow coming from the jet nozzle. During exhalation the jet flow is suspended and the valve returns in its close state. On the surface of the valve a plurality of holes ensure that the exhaled gas can be evacuated to the ambient by building a back pressure sufficient to maintain PEEP in the patient's airways. A range of different valves can be realized so that different PEEP values can be achieved. Color coding can be used to identify the PEEP value. The perforated flapper valve is just one of several modalities which may be used to achieve the same function. Along these lines, the perforations on the flapper could be replaced by grooves on the sealing surface of either the valve or the seat of the throat. The umbrella valve can be used in a similar fashion, with or without orifices/holes within the same.

The present invention is best understood by reference to the following detailed description when read in conjunction with the accompanying drawings.

BRIEF DESCRIPTION OF THE DRAWINGS

These, as well as other features of the present invention, will become more apparent upon reference to the drawings wherein.

Common reference numerals are used throughout the drawings and detailed description to indicate like elements.

DETAILED DESCRIPTION OF THE INVENTION

Figure 1:
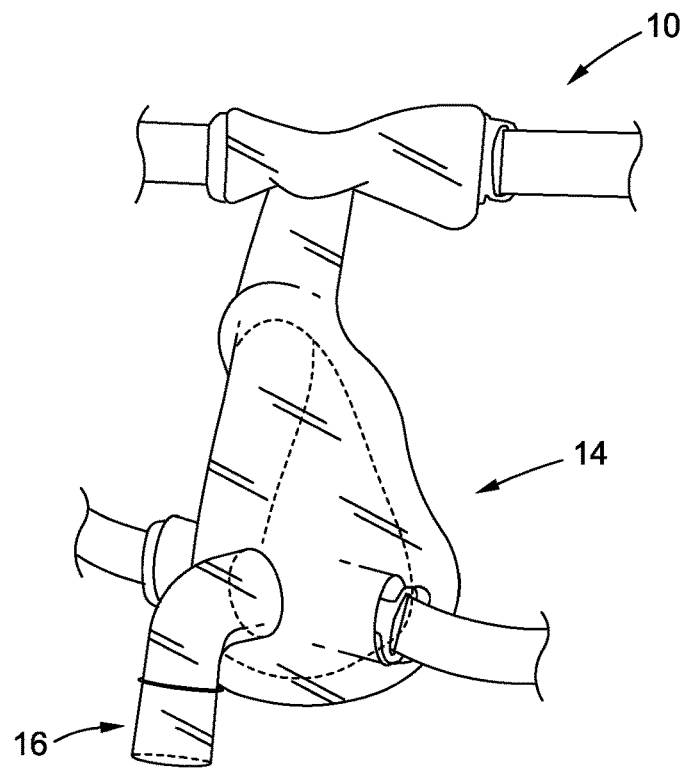
FIG. 1 is a front perspective view of an exemplary prior art mask suitable for use in conjunction with any jet pump adaptor constructed in accordance with the present invention.
Figure 2:
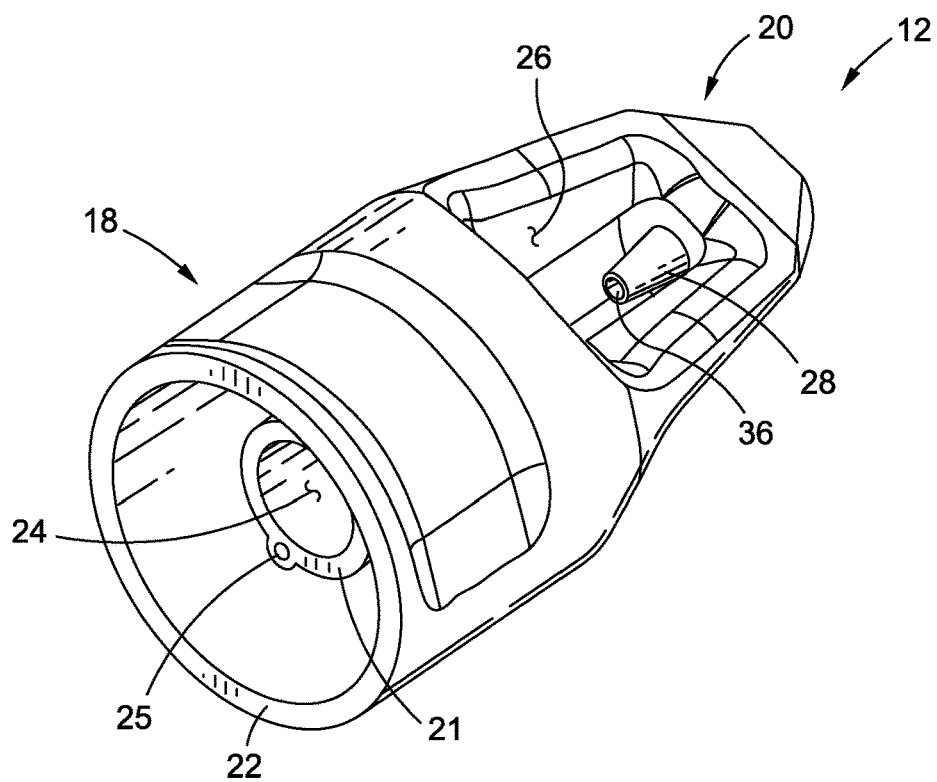
FIG. 2 is a front perspective view a jet pump adaptor constructed in accordance with a first embodiment of present invention.
Figure 3:
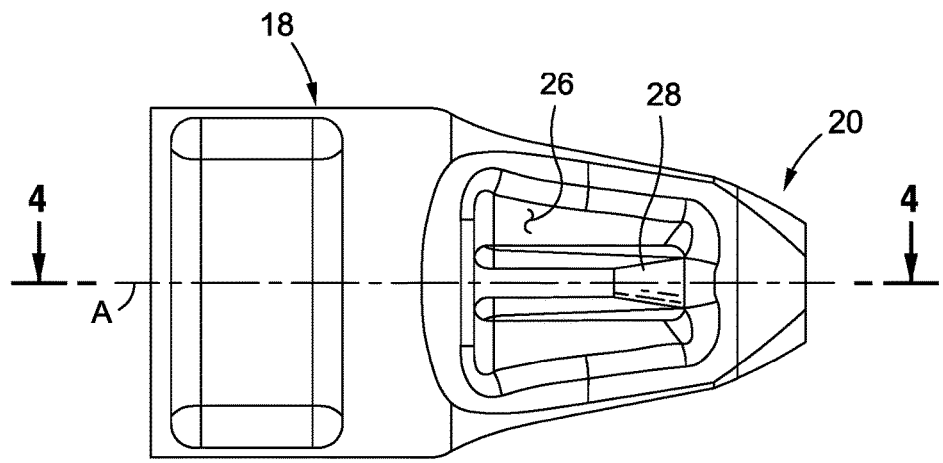
FIG. 3 is a bottom view of the jet pump adaptor shown in FIG. 2.

Referring now to the drawings for which the showings are for purposes of illustrating preferred embodiments of the present invention only, and not for purposes of limiting the same, FIG. 1 depicts an exemplary prior art patient interface or mask 10 suitable for use with the jet pump adaptor 12 of the present invention, as will be described in more detail below. As indicated above, the preferred patient interface used in conjunction with the adaptor 12 of the present invention is a non-vented (or non-leak) nasal mask or full face mask, the mask 10 being a non-vented full-face mask. In this regard, the mask 10 comprises a body portion 14 which is sized and configured to cover the nose and mouth of a patient. In addition to the body portion 14, the mask 10 includes a tubular connector portion 16 which is fluidly coupled to the body portion 14. As also indicated above, though the adaptor 12 is preferably used in conjunction with the non-vented mask 10, the same may also be used in conjunction with a traditional vented nasal mask or full face mask.

Figure 4:
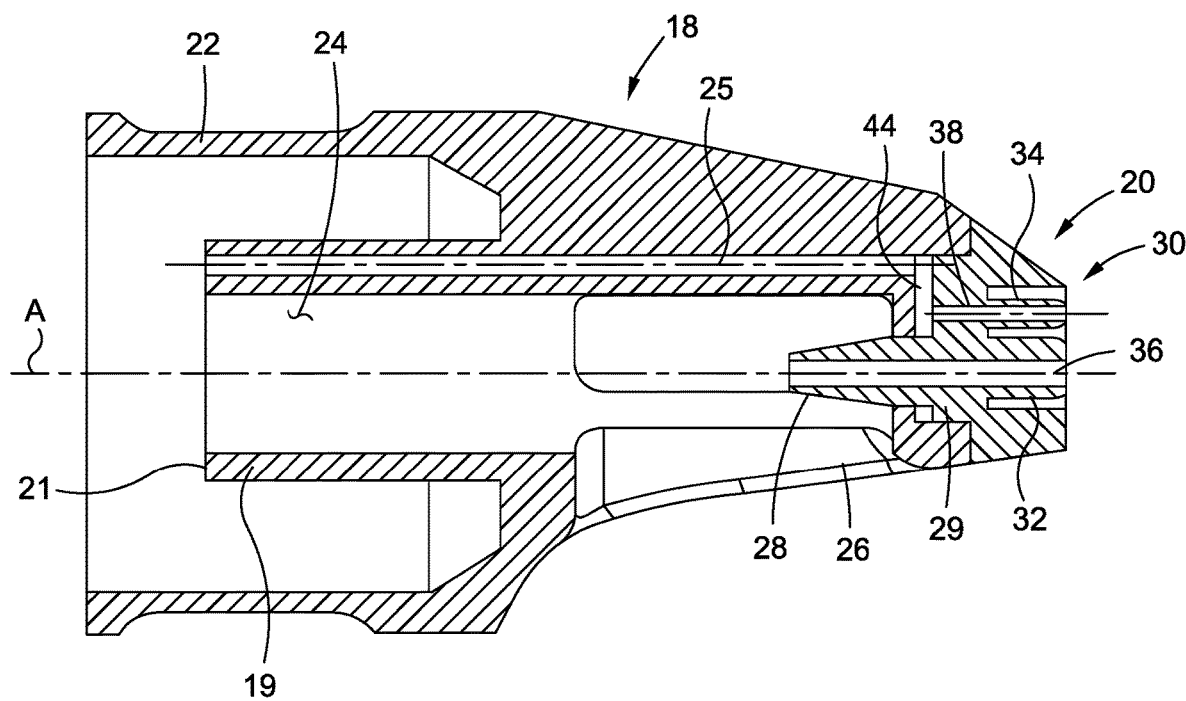
FIG. 4 is a cross-sectional view taken along line 4-4 of FIG. 3.
Figure 5:
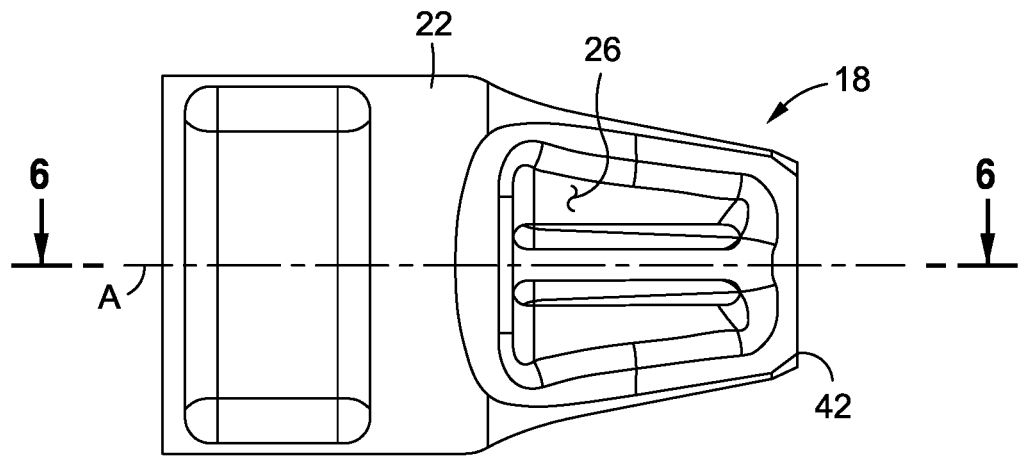
FIG. 5 is a bottom view of the base element of the jet pump adaptor shown in FIGS. 2-4.
Figure 6:
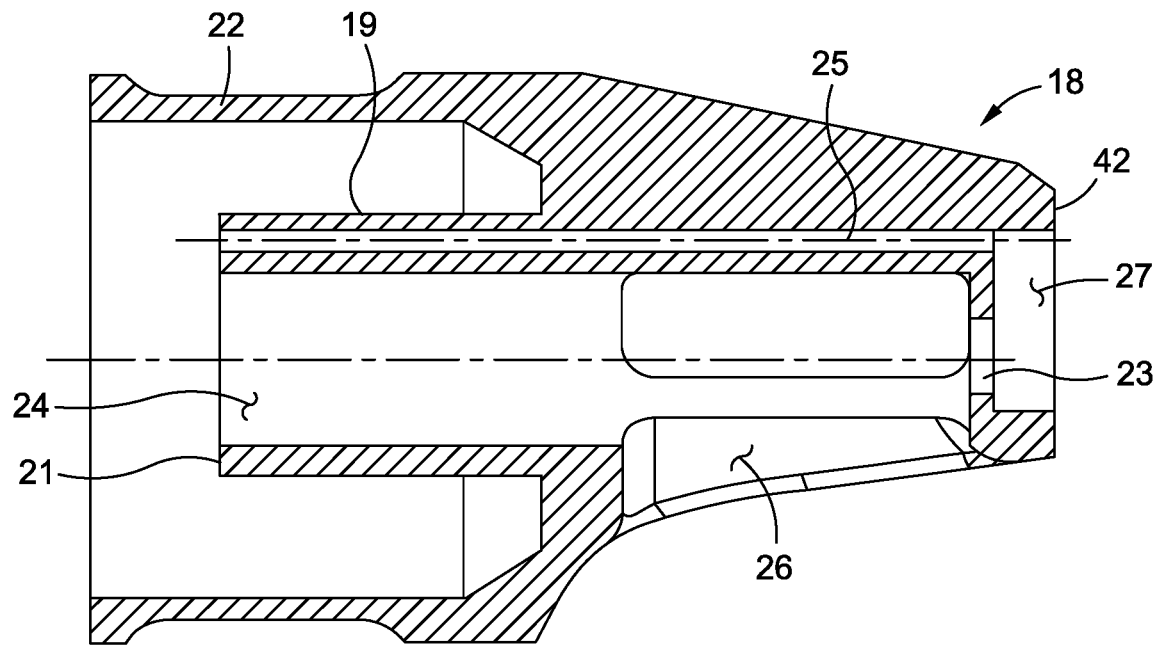
FIG. 6 is a cross-sectional view taken along line 6-6 of FIG. 5.
Figure 7:
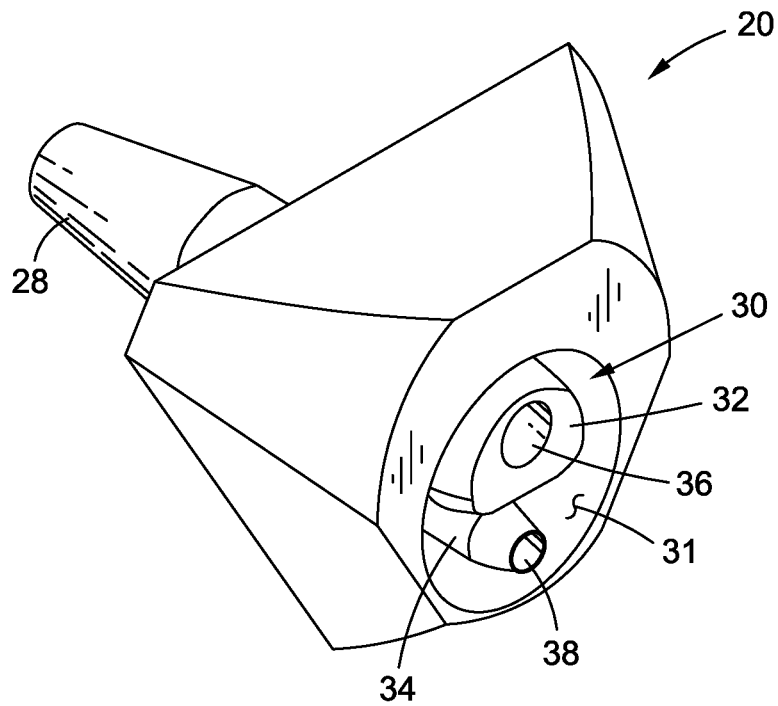
FIG. 7 is a rear perspective view of the nozzle element of the jet pump adaptor shown in FIGS. 2-4.
Figure 8:
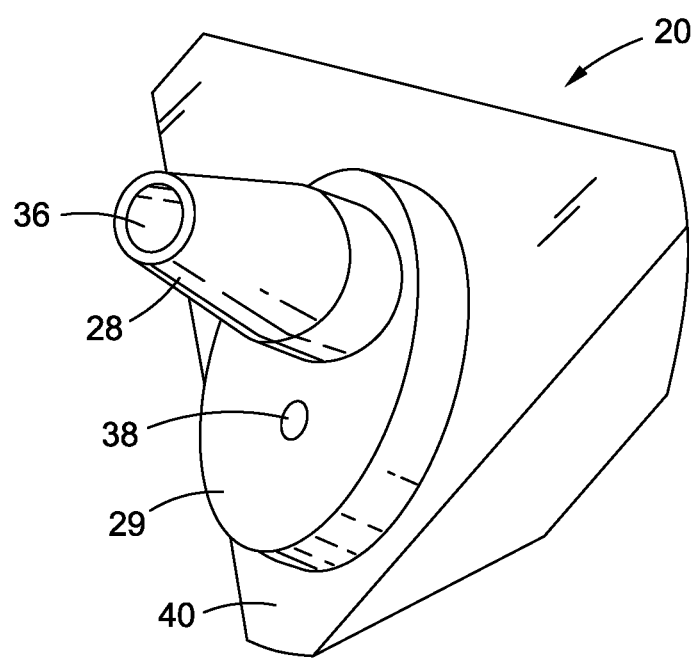
FIG. 8 is a front perspective view of the nozzle element of the jet pump adaptor shown in FIGS. 2-4.

The adaptor 12 as constructed in accordance with a first embodiment of the present invention is shown with particularity in FIGS. 2-8. The adaptor 12 comprises of base element 18 (as shown in FIGS. 5 and 6) and a nozzle element 20 (as shown in FIGS. 7 and 8) which are operatively coupled to each other. More particularly, the nozzle element 20 may be rigidly, rotatably, or threadably connected to the base element 18 in a manner which will be described in more detail below, the rotatable and threadable connections allowing for the selective rotation of the nozzle element 20 relative to the base element 18.

As is best seen in FIGS. 2-6, the base element 18 includes a connector 22 which is preferably a standard 22 mm ISO taper connector. In this regard, due to its preferred structural attributes, the connector 22 allows for the releasable attachment of the base element 18, and hence the adaptor 12, to any standard ventilation mask, including the exemplary mask 10 shown in FIG. 1. In this regard, by way of example, the connector 22 is adapted to receive and releasably accommodate the connector portion 16 of the mask 10. In addition to the connector 22, the base element 18 defines a throat 24. More particularly, the throat 24 is defined by a tubular wall 19 which has a generally circular cross-sectional configuration and protrudes into the interior of the connector 22, as seen in FIGS. 4 and 6. The configuration shown in FIGS. 4 and 6, wherein the tubular wall 19 protrudes into the interior of the connector 22, is exemplary only, and is used to reduce the overall length of the adaptor 12. Adaptors for ISO tapers smaller than 22 mm may have a different architecture and, more particularly, may be longer than the adaptor 12. The wall 21 defines a distal end or rim 21. That end of the throat 24 circumvented by the rim 21 fluidly communicates with the interior of the connector 22. The base element 18 also defines at least one air entrainment port 26 which fluidly communicates with the throat 24. More particularly, as is also apparent from FIG. 6, the entrainment port 26 facilitates the fluid communication of the throat 24 with ambient air. Still further, the base element 18 defines an elongate pressure sensing line or lumen 25 which extends in side-by-side relation to, but is fluidly isolated from, the throat 24. Like the throat 24, one end of the pressure sensing lumen 25 terminates at the rim 21 of the wall 19 and fluidly communicates with the interior of the connector 22. In this regard, a portion of the pressure sensing lumen 25 extends through the wall 19. The opposite end of the pressure sensing lumen 25 terminates at a recess 27 which is formed within that end of the base element 18 opposite the end defined by the connector 22. The use of the recess 27 will be described in more detail below. In the base element 18, an aperture or opening 23 extends between the throat 24 and the bottom, innermost surface of the recess 27.

As best seen in FIGS. 2-4 and 7-8, the nozzle element 20 includes a jet nozzle 28 and a connector 30 which is adapted to facilitate the fluid coupling of the nozzle element 20, and hence the adaptor 12, to a bi-lumen tube of a patient circuit including the adaptor 12 and mask 10. Though not shown, such bi-lumen tube defines both a gas delivery lumen and a sensing lumen which is fluidly isolated from the gas delivery lumen. The jet nozzle 28 has a generally frusto-conical external configuration or shape, and protrudes from a circularly configured mandrel portion 29 of the nozzle element 20. The connector 30 of the nozzle element 20 includes both a tubular gas delivery port 32 and a tubular pressure sensing port 34 which, as best seen in FIG. 7, reside within a common recess 31. The recess 31 is formed within that end of the nozzle element 20 opposite that defined by the distal end the jet nozzle 28 protruding from the mandrel portion 29.

In the adaptor 12, the recess 27 formed within the base element 18 has a configuration which is complementary to that of the mandrel portion 29 of the nozzle element 20. In accordance with the present invention, three (3) different attachment modes may be achieved between the base and nozzle elements 18, 20. In a first attachment mode, the base and nozzle elements 18, 20 are rigidly secured to each other. More particularly, the circularly configured mandrel portion 29 is advanced into the complementary, circularly configured recess 27 and secured therein by way of, for example, glue, a weld, or a press fit. In a second attachment mode, the base and nozzle elements 18, 20 are rotatably connected to each other. In this regard, the rotatable connection of the nozzle element 20 to the base element 18 is facilitated by the slidable receipt of the circularly configured mandrel portion 29 into the complementary, circularly configured recess 27. In a third attachment mode, the base and nozzle elements 18, 20 are threadably connected to each other. Though not shown, the threadable connection of the nozzle element 20 to the base element 18 may be facilitated by the engagement of male threads formed on the circularly configured mandrel portion 29 to complementary female threads formed within the circularly configured recess 27. As is seen in FIG. 4, in any of the aforementioned attachment modes, the advancement of the mandrel portion 29 into the recess 27 is limited by the abutment of a shoulder 40 defined by the nozzle element 20 and circumventing the mandrel portion 29 thereof against an end surface 42 defined by the base element 18 and circumventing the recess 27 form therein. Both prior to and when such abutment occurs during the advancement of the mandrel portion 29 into the recess 27, an annular gap or channel 44 of a prescribed width is defined between the outer, distal surface of the mandrel portion 29 and the bottom, innermost surface defined by the recess 27.

The advancement of the mandrel portion 29 into the recess 27 facilitates the concurrent advancement of the jet nozzle 28 through the opening 23. In this regard, as further seen in FIG. 4, in the opening 23 is preferably formed to have a diameter which is only slightly less than that of the base of the jet nozzle 28 which extends to the outer, distal surface of the mandrel portion 29. This is done so that when the jet nozzle 28 is advanced through the opening 23, a gas-tight (albeit slidable or rotatable) coupling is formed by the interference between the jet nozzle 28 and the circumferential surface of the base element 18 defining the opening 23. A similar gas-tight coupling or fit is also preferably achieved between the circumferential outer surface defined by the mandrel portion 29 and the circumferential inner surface defined by the recess 27 when the mandrel portion 29 is advanced into the recess 27. When the shoulder 40 is abutted against the end surface 42, the jet nozzle 28, by virtue of having been advanced through the complementary opening 23, protrudes into the throat 24 of the base element 18 and is visible within the entrainment port 26. The aforementioned channel 44 circumvents the base of the jet nozzle 28. It is contemplated that the opening 23 may be outfitted with a seal, the configuration of which provides for the aforementioned gas-tight coupling of the jet nozzle 28 to the base element 18, yet allows for the rotation of the jet nozzle 28 within the opening 23 in the event either the rotatable or threadable attachment modes between the base and nozzle elements 18, 20 are implemented in the adaptor 12.

In the nozzle element 20, the jet nozzle 28 and the gas delivery port 32 of the connector 30 collectively define a gas delivery line or lumen 36 which fluidly communicates with the throat 24 of base element 18 when the nozzle element 20 is coupled to the base element 18. As is also most easily seen in FIG. 4, when the nozzle element 20 is connected to the base element 18, the gas delivery lumen 36 and the throat 24 extend along a common axis A, with the axis of the pressure sensing lumen 25 of the base element 18 extending in spaced, generally parallel relation to such axis A. The gas delivery lumen 36 and the throat 24 collectively define a gas delivery conduit of the adaptor 12. The gas delivery lumen 36, and hence the gas delivery conduit, is placeable into fluid communication with the gas delivery lumen of the bi-lumen tube in a manner which will be described in more detail below.

As best seen in FIGS. 4, 7 and 8, the pressure sensing port 34 of the connector 30 partially defines a pressure sensing line or lumen 38 of the nozzle element 20. That end of the pressure sensing lumen 38 opposite the end defined by the pressure sensing port 34 terminates at the outer, distal surface of the mandrel portion 29, as seen in FIG. 8. When the nozzle element 20 is connected to the base element 18, the pressure sensing lumen 36 also extends in spaced, generally parallel relation to the axis A, with the pressure sensing lumens 25, 38 and intervening channel 44 collectively defining a pressure sensing conduit of the adaptor 12. Since, as indicated above, the pressure sensing lumen 25 of the base element 18 is formed to fluidly communicate with the recess 27 thereof, such pressure sensing lumen 25 thus fluidly communicates with the channel 44 when the nozzle element 20 is connected to the base element 18. Similarly, since the channel 44 is annular and circumvents the jet nozzle 28 as indicated above, the pressure sensing lumen 38 is maintained in a constant state of fluid communication with the channel 44, irrespective of the orientation of the nozzle element 20 relative to the base element 18 if it is rotatably or threadably connected thereto. As such, the integrity of the pressure sensing conduit of the adaptor 12 collectively defined by the pressure sensing lumens 25, 38 and intervening channel 44 is not compromised by any rotation of the nozzle element 20 relative to the base element 18 during use of the adaptor 12, assuming that the nozzle element 20 is not rigidly attached to the base element 18. Further, irrespective of whether the nozzle element 20 is rigidly, rotatably or threadably connected to the base element 18, the inclusion of the channel 44 in the pressure sensing conduit allows the pressure sensing lumen 25 to be disposed further radially outward relative to the axis A in comparison to the pressure sensing lumen 38 while being maintained in a constant state of fluid communication therewith by the channel 44. The pressure sensing lumen 38, and hence the pressure sensing conduit, is placeable into fluid communication with the pressure sensing lumen of the bi-lumen tube in a manner which will be also described in more detail below.

It is contemplated that the adaptor 12 as described above will be integrated into a patient circuit wherein a main delivery tube, and more particularly the aforementioned preferred bi-lumen tube, is used to facilitate the fluid communication between a flow generator or ventilator and the adaptor 12 (and hence the mask 10 coupled to the adaptor). More particularly, the bi-lumen tube is advanced into the recess 31 such that the gas delivery port 32 of the connector 30 is coaxially aligned with an advanced into the gas delivery lumen of the bi-lumen tube. Similarly, the pressure sensing port 34 of the connector 30 is coaxially aligned with and advanced into the pressure sensing lumen of the bi-lumen tube. As will be recognized, is contemplated that the cross-sectional configuration of the gas delivery lumen of the bi-lumen tube will be complementary to the configuration of the gas delivery port 32 of the connector 30 such that the gas delivery port 32 is frictionally maintainable within the gas delivery lumen of the bi-lumen tube upon being advanced therein. Similarly, the cross-sectional configuration of the pressure sensing lumen of the bi-lumen tube will preferably be complementary to the configuration of the pressure sensing port 34 of the connector 30 such that the pressure sensing port 34 is frictionally maintainable within the pressure sensing lumen of the bi-lumen tube upon be advanced therein. Bonding agents such as glue, or other techniques, can also be used to retain the bi-lumen tube within the nozzle element 20. As is further seen in FIG. 7, the distal end portion of the pressure sensing port 34 preferably has a tapered configuration to assist in the advancement thereof into the pressure sensing lumen of the bi-lumen tube. As will be recognized by those of ordinary skill in the art, the advancement of the bi-lumen tube into the recess 31 is limited by the abutment of the corresponding end of such bi-lumen tube against the bottom, innermost surface defined by the recess 31.

In the adaptor 12, the gas delivery conduit (as defined by the gas delivery lumen 36 through the jet nozzle 28 and the throat 24) in combination with the entrainment port 26 creates a jet pump when pressurized gas is introduced into the gas delivery conduit by the bi-lumen tube coupled to the adaptor 12. In a patient circuit outfitted with the adaptor 12, is contemplated that such jet pump will be able to generate a maximum pressure of pressure of about 30 cm H2O (and preferably about 20 cm H2O), and a peak flow of about 100 l/min (and preferably 60 l/min). Pressure and flow are generated in a manner wherein a breathable gas (O2, air, or other mixtures of breathable gas) is delivered to the jet nozzle 28 of the jet pump and ambient air is entrained through the entrainment port 26. The flow of the pressurized gas mixture (including the entrained air) is delivered to the patient through the connector 22 and the mask 10 coupled thereto. The gas exhaled by the patient may be exhausted through the entrainment port 26. Though not shown in FIGS. 2-8, is contemplated that a heat and moisture exchange device (HME) and/or an anti-bacterial filter can be connected between the jet pump and the connector portion 16 of the mask 10.

It is contemplated that in the adaptor 12, the nozzle element 20 can be molded with anyone of a multiplicity of different sizes of the jet nozzle 28 in order to selectively change the performance of the jet pump (e.g., more or less pressure or flow). Further, it is contemplated that the nozzle element 20 may be color-coded so that the user can easily understand the jet pump performance provided thereby. Along these lines, it is further contemplated that the adaptor 12 may be configured such that the nozzle element 20 thereof may be switched out to one having an alternative configuration so as to selectively modify the performance of the adaptor 12.

Figure 9:
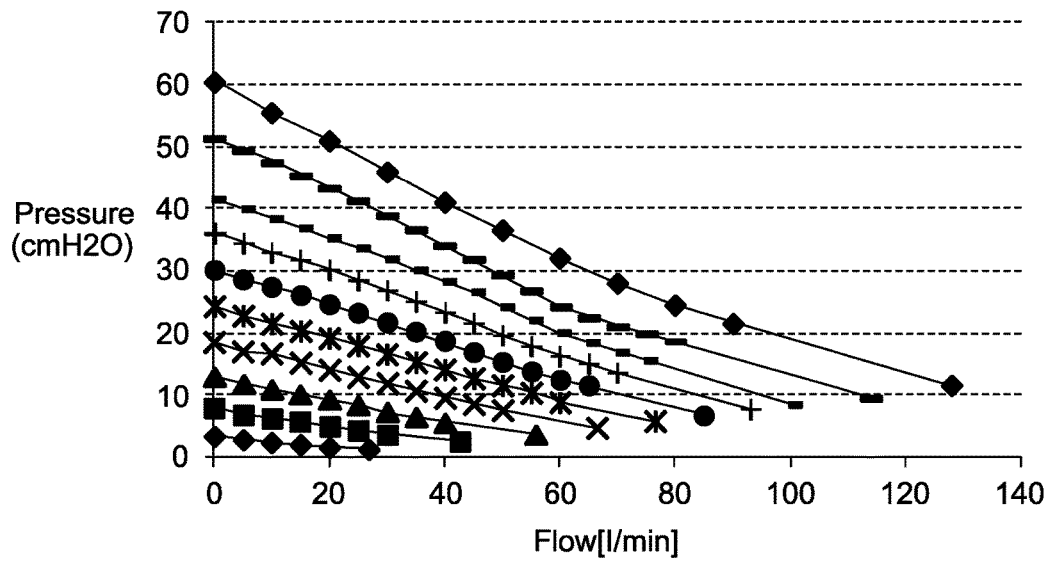
FIG. 9 is a graphical representation of typical characteristic curves corresponding to the functionality of the jet pump adaptor of the first embodiment, the curves being parameterized with jet flow.

In the adaptor 12, the performance of the jet pump is predominately driven by the geometric factors of the size of the jet nozzle 28 (nozzle size), the size of the throat 24 (throat size), and the distance from the distal end of the jet nozzle 28 to the end of the throat 24 as circumvented by the base of the wall 19 disposed furthest from the rim 21 (nozzle-to-throat distance). In the adaptor 12, it is contemplated that the throat size will be fixed, and that if the base and nozzle elements 18, 20 are rigidly or rotatably secured to each other, the nozzle-to-throat distance will be fixed as well. On the other hand, if the base and nozzle elements 18, 20 are threadably secured to each other, the nozzle-to-throat distance may be varied to selectively modify the performance characteristics of the jet pump, as will be described in more detail below. However, even the case of a rigid or rotatable connection between the base and nozzle elements 18, 20, the nozzle size may be varied as indicated above, so as to selectively adjust or modify the performance of the jet pump. Along these lines, it is further contemplated that if the base and nozzle elements 18, 20 are rigidly or rotatably secured to each other, an even wider range of variation in the jet pump range can be achieved by pairing every nozzle element 12 with a base element 18 in which the throat size and the nozzle-to-throat distance have been designed to optimize performance. However, a similar range of increased performance can also be achieved by only varying nozzle size and having variable jet flow. This is possible when using the adaptor 12 in a non-invasive open ventilation system instead of connecting it to a fixed flow source. Along these lines, the outfitting of the adaptor 12 with the pressure sensing conduit allows for the implementation of the adaptor 12 in, for example, a close pressure loop control with an non-invasive open ventilation system. The range of variability of performance of the jet pump with the jet flow is depicted graphically in FIG. 9. The graph is a typical characteristic curve of the jet pump where the curves are parameterized with the jet flow, and demonstrate that increasing the jet flow increases the jet pump performances. The embodiment of the adaptor 12 shown and described above, as well as those embodiments described below, can also be used with a flow regulator instead of within a non-invasive open ventilation system. This practically means that the user will select a fixed flow value for the jet nozzle 28, with the performances of the jet pump being represented by a single line corresponding to the set jet flow in the graph of FIG. 9.

Though the structural and functional features of the adaptor 12 as assembled using the attachment mode wherein the base and nozzle elements 18, 20 are rigidly secured to each other could be implemented in a unitary construction rather than a two-piece construction, the use of the two-piece construction provides certain manufacturing advantages and economies. More particularly, by having a two-piece construction, a generic base element 18 may be provided, with any one of a multiplicity of nozzle elements 20 each having differently configured jet nozzles 28 being rigidly secured to the base element 18 in the aforementioned manner. As indicated above, the nozzle elements 20 may be color-coded, thus providing a visual indication of the performance features of the adaptor 12 even subsequent to the rigid attachment of the base and nozzle element 18, 20 to each other.

As indicated above, the base and nozzle elements 18, 20 may be threadably secured to each other to allow for selective variations or adjustments in the nozzle-to-throat distance for purposes of modifying the performance characteristics of the jet pump. In this regard, in the threadable connection attachment mode described above, the rotation of the nozzle element 20 in a clockwise direction relative to the base element 18 would effectively shorten the nozzle-to-throat distance. Conversely, the rotation of the nozzle element 20 in a counter-clockwise direction relative to the base element 18 would effectively lengthen the nozzle-to-throat distance.

Figure 10:
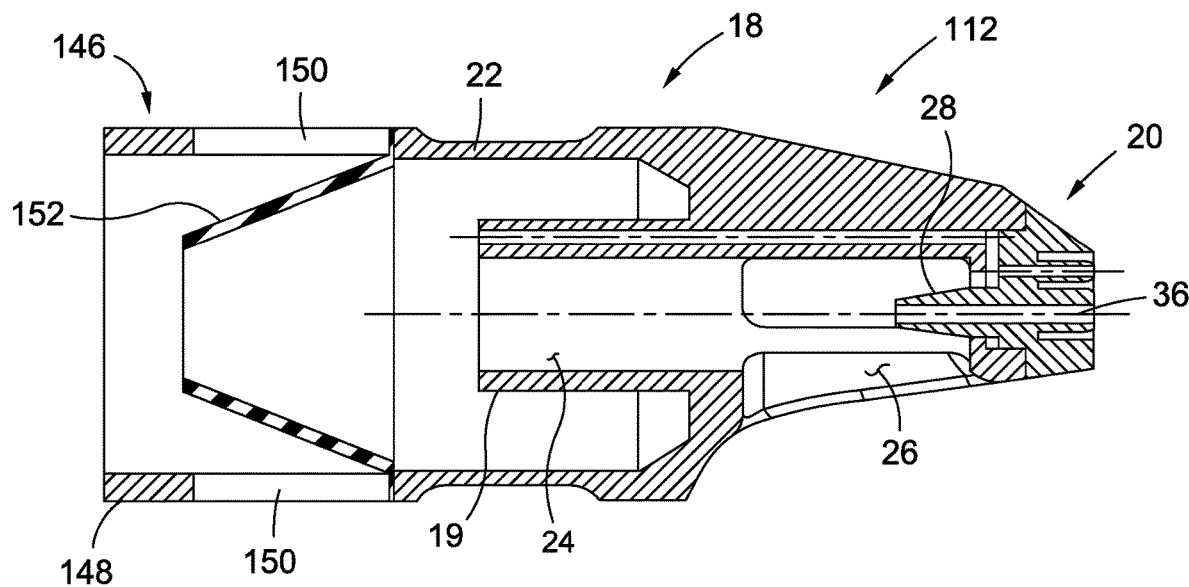
FIG. 10 is a cross-sectional view a jet pump adaptor constructed in accordance with a second embodiment of present invention.

Referring now to FIG. 10, there is shown an adaptor 112 constructed in accordance with a second embodiment of the present invention. The adaptor 112 comprises the adaptor 12 shown in FIGS. 2-8 and described above, but enhanced in a manner wherein the jet pump is equipped with an exhalation or anti-asphyxia valve (AAV) 146 in order to reduce the back pressure during exhalation. More particularly, the valve 146 may be used to decrease expiratory pressure in the case when the throat 24 of the jet pump is too small or in case of failure of the ventilator or gas source.

In the adaptor 112, the valve 146 comprises a generally cylindrical, tubular housing 148 which includes at least one, and preferably a pair of exhalation ports 150 formed therein. The housing 148 is attached to the connector 22 of the base element 18, and is releasably engageable to the connector portion 16 of the mask 10. The valve 146 further comprises a resilient, conical diaphragm 152 which is disposed within the interior of the housing 148, and is selectively movable between open and closed positions relative thereto. As seen in FIG. 10, the end of the diaphragm 152 of greatest diameter is defined by a radially extending flange portion thereof which is captured between the housing 148 and the distal end or rim of the connector 22 of the base element 18.

When there is positive pressure and flow in the jet pump of the adaptor 112, the diaphragm 152 is stretched to its closed position to seal against (and thus close or block) the exhalation ports 150 (which are separate from the entrainment port 26). Conversely, when the jet pump is not activated (i.e. during exhalation), the diaphragm 152 moves to the open position shown in FIG. 10, thus unblocking the exhalation ports 150. The same function can be achieved thorough the use of a flapper valve as an alternative to the aforementioned diaphragm 152.

Figure 11:
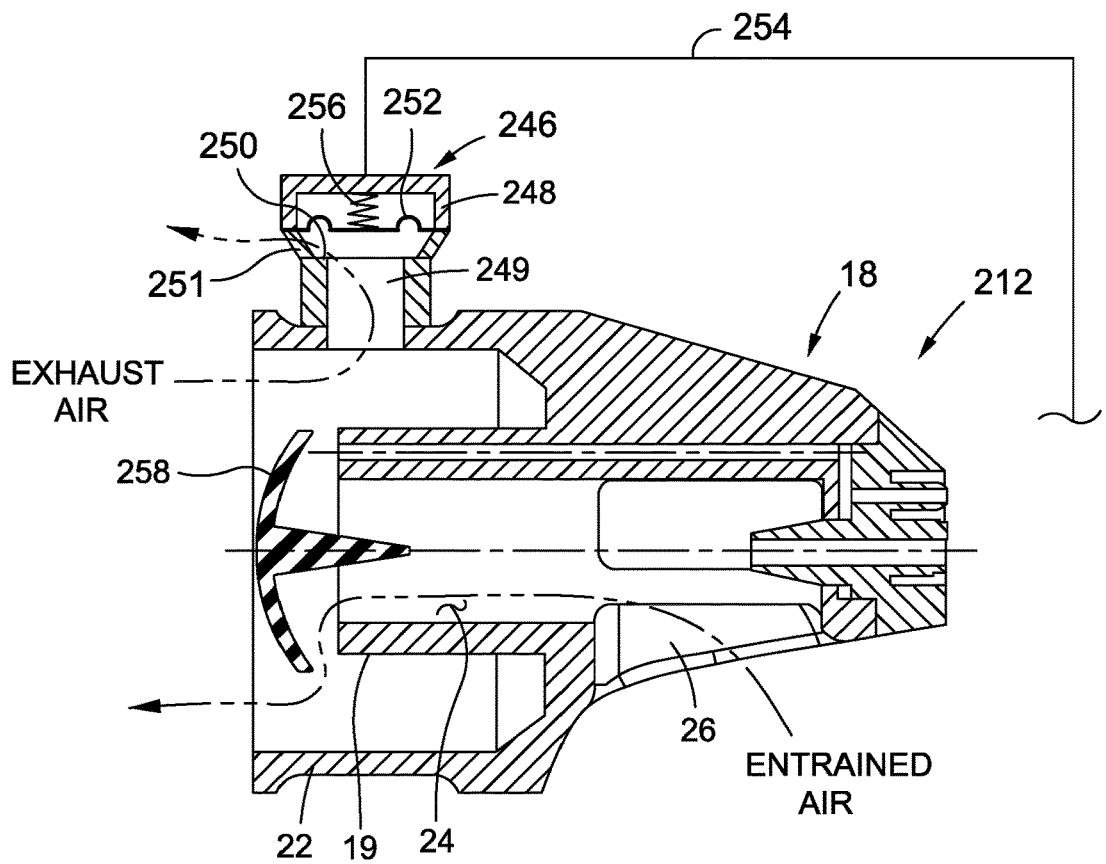
FIG. 11 is a cross-sectional view a jet pump adaptor constructed in accordance with a third embodiment of present invention.

Referring now to FIG. 11, there is shown an adaptor 212 constructed in accordance with a third embodiment of the present invention. The adaptor 212 comprises the adaptor 12 shown in FIGS. 2-8 and described above, but enhanced in a manner wherein the jet pump is equipped with a exhalation/positive end expiratory pressure (PEEP) valve. More particularly, the jet pump of the adaptor 212 comprises a piloted exhalation valve 246.

The valve 246 comprises a housing 248 which is attached to the connector 20 of the base element 18. As seen in FIG. 11, the housing 248 defines a hollow interior chamber 249 which fluidly communicates with the interior of the connector 20. The housing 248 has a generally circular cross-sectional configuration, with the interior chamber 249 thereof (when viewed from the perspective shown in FIG. 11) defining a lower section which protrudes from the connector 20 and is of a first diameter, and a distal upper section which is of a second diameter exceeding the first diameter. The lower and upper sections of the interior chamber 249 are separated from each other by a continuous, annular shoulder 250 defined by the housing 248.

Disposed within the upper section of the interior chamber 249 and extending diametrically there across is a resilient diaphragm 252 of the valve 246. When viewed from the perspective shown in FIG. 11, the diaphragm 252 effectively segregates the upper section of the interior chamber 249 into an upper region and a lower region, the lower region extending to the shoulder 250. The housing 248 includes at least one exhaust port 251 which is formed therein and fluidly communicates with the lower region of the upper section of the interior chamber 249. The upper region of the upper section of the interior chamber 249 is preferably placed into fluid communication with the gas delivery lumen 36 or the gas delivery lumen of the bi-lumen tube of the exemplary patient circuit including the adaptor 212 via a pressure line 254 extending therebetween.

In the valve 246, the diaphragm 252 is selectively movable between an open position (shown in FIG. 11) and a closed position. When the diaphragm 252 is in its open position, an open fluid flow path between the interior of the connector 20 and ambient air is defined by, in succession, the lower section of the interior chamber 249, the lower region of the upper section of the interior chamber 249, and the exhaust port 251 formed in the housing 248. When the diaphragm 252 is actuated to its closed position, the same is effectively seated and sealed against the shoulder 250 in a manner effectively blocking the exhaust port 251 from fluid communication with the lower section of the interior chamber 249, and hence the interior of the connector 20. The valve 246 may further optionally include a spring 256 which is disposed within the upper region of the upper section of the interior chamber 249, and extends between the approximate center of the diaphragm 252 and a corresponding section of the interior surface of the housing 248.

Due to its inclusion of the diaphragm 252, the valve 246 of the adaptor 212 can be piloted between on/off states or may be piloted in a proportional fashion to achieve positive end expiratory pressure (PEEP) control by using the pressure in the gas delivery lumen 36 or the gas delivery lumen of the aforementioned bi-lumen tube of the patient circuit that feeds the jet nozzle 28 via the gas delivery lumen 36. As indicated above, this pressure is delivered is to the valve 246, and in particular the diaphragm 252 thereof, by the pressure line 254. In this way, the valve 246 opens and closes in sync with the breathing pattern of the patient. During inhalation, when the jet flow is delivered to the jet pump of the adaptor 212, the diaphragm 252 of valve 246 is closed by the high pressure in the gas delivery lumen 36 or the gas delivery lumen of the aforementioned bi-lumen tube. During exhalation there is either no flow delivered by the jet nozzle 28 (and hence no pressure in the gas delivery lumen 36) and the diaphragm 252 of the valve 246 opens, or a small flow and pressure can be maintained in the gas delivery lumen 36 so that the jet pump can create back pressure in the throat 24 against exhalation and the valve 246 can be servoed with positive pressure to vary the resistance. This latter system results in a controllable PEEP value and requires a careful sizing and matching of the jet pump performances at low flow and the PEEP characteristic of the valve 246. This is made easier using a closed loop control over the pressure sensed by the pressure sensing lumen of the patient circuit comprising the pressure sensing conduit of the adaptor 212 and the pressure sensing lumen of the bi-lumen tube. The valve 246 can also be used as a PEEP valve by using the spring 256 (if included) to maintain PEEP and the pilot line 254 to facilitate the closure of the diaphragm 252 during inhalation. In this embodiment the PEEP value can be adjusted by changing the pre-load of the spring 254 (e.g., by rotating a portion of the housing 248). Optionally, for a better PEEP control, a non-return valve 258 (e.g. an umbrella valve) can be used to close the throat 24 of the jet pump throat during exhalation. As shown in FIG. 11, the valve 258 preferably resides within the interior of the connector 22, and is selectively engageable to the rim 21 of the wall 19 in a manner which will effectively close the corresponding end of the throat 24.

Figure 12:
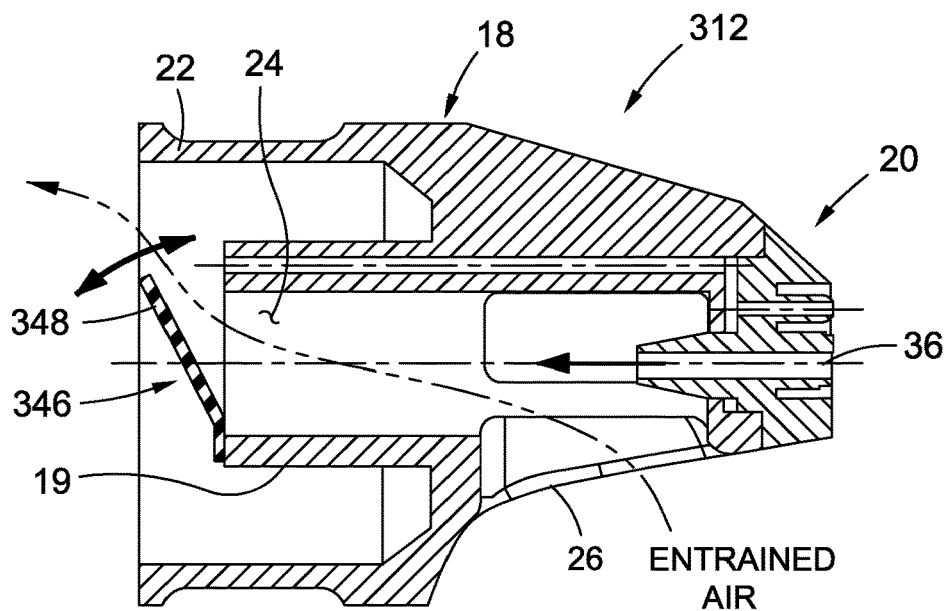
FIG. 12 is a cross-sectional view a jet pump adaptor constructed in accordance with a fourth embodiment of present invention.

Referring now to FIG. 12, there is shown an adaptor 312 constructed in accordance with a fourth embodiment of the present invention. The adaptor 312 also comprises the adaptor 12 shown in FIGS. 2-8 and described above, but enhanced in a manner wherein the jet pump is equipped with a fixed PEEP valve in the shape of, for example, a flapper valve 346 cooperatively engaged to the wall 19 at the rim 21 thereof, and thus disposed at the end of the throat 24. The flapper valve 346 is normally closed (i.e., rests against the throat 24 of the jet pump, and in particular the rim 21 of the wall 19) and opens during inhalation (as shown in FIG. 12) when positive pressure and flow are established by the jet flow coming from the gas delivery lumen 36 via the jet nozzle 28. The flapper valve 346 also opens in the case of a failure of the source of breathable gas as a result of a negative pressure being established on the patient side of the flapper valve 346 due to the respiratory effort of the patient. During exhalation, the jet flow is suspended and the flapper valve 346 returns in its closed state. The flapper valve 346 preferably includes a plurality of holes or perforations 348 therein to ensure that the exhaled gas can be evacuated to the ambient via the entrainment port 26 by building a back pressure sufficient to maintain PEEP in the patient's airways. Any one of a range of flapper valves 346 have differing configurations can be selectively used so that different PEEP values can be achieved in the adaptor 312. Along these lines, color coding can be used to identify the PEEP value corresponding to the particular flapper valve 346 integrated into the adaptor 312. The perforated flapper valve 346 is just one of several modalities which may be used to achieve the same function. Along these lines, the perforations 348 in the flapper valve 346 could be replaced by grooves on the sealing surface thereof, or grooves formed within the seat of the throat 24, i.e., the rim 21 which circumvents the distal end of the throat 24. The same functions may also be achieved by using, for example, and umbrella valve or any other non-return valve having a design which lends itself to the implementation of the working principle exemplified by the adaptor 312.

As indicated above, in each of the above-described embodiments, the jet nozzle 28, in combination with the throat 24, the entrainment port 26 and the gas delivery lumen 36, creates a jet pump within the adaptor 12, 112, 212, 312. As explained above, the present invention contemplates the use of various techniques to selectively vary the performance attributes of the jet pump as may be need to provide a prescribed therapeutic treatment. However, the jet pump, in any embodiment, is operative to provide a prescribed level of pressure and flow to the mask 10 with the use of a small diameter main gas delivery tube (e.g., the aforementioned bi-lumen tube) within the patient circuit.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure.

What is claimed is:

1. An adaptor for fluidly coupling a flow generator to a ventilation mask in a respiratory assistance system, the adaptor comprising:
   a connector which is fluidly connectible to the ventilation mask and defines an interior;
   a tubular wall which protrudes into the interior of the connector and at least partially defines a throat, the tubular wall having a distal end which fluidly communicates with the interior of the connector and a proximal end which is opposite the distal end;
   at least one entrainment port in open fluid communication with ambient air, the at least one entrainment port being at least partially defined by an aperture in the tubular wall between the distal end and the proximal end;
   a jet nozzle in fluid communication with a gas delivery lumen of a main gas delivery tube that is connectable to the flow generator, the jet nozzle having a distal tip that is positioned within the throat at a distance from the distal end of the tubular wall to fluidly communicate gas into the throat with at least a portion of the at least one entrainment port between the distal tip of the jet nozzle and the distal end of the tubular wall, such that when gas is flowed through the gas delivery lumen, out the jet nozzle, and into the throat, ambient air is entrained through the at least one entrainment port; and
   a pressure sensing lumen in fluid communication with a sensing lumen of the main gas delivery tube via an annular gap, the pressure sensing lumen extending through the adaptor in side-by-side relation to, and not within, the throat.

2. The adaptor of claim 1 wherein the connector is sized and configured to allow for releasable attachment of the adaptor to the ventilation mask.

3. The adaptor of claim 2 wherein the connector is a standard 22 mm ISO taper connector which allows for the releasable attachment of the adaptor to the ventilation mask.

4. The adaptor of claim 1 wherein the annular gap circumvents a portion of the jet nozzle; with the pressure sensing lumen, the sensing lumen of the main gas delivery tube, and the annular gap being fluidly isolated from gas flowed through the gas delivery lumen and into the throat throughout 360° rotation of the jet nozzle relative to the throat.

5. The adaptor of claim 1 further comprising a second connector which allows for releasable attachment of the adaptor to the main gas delivery tube.

6. The adaptor of claim 5 wherein the second connector comprises:
   a gas delivery port in fluid communication with the jet nozzle; and
   a pressure sensing port which at least partially defines the pressure sensing lumen;
   the gas delivery and pressure sensing ports at least partially residing within a common recess of the adaptor and extending in side-by-side relation to each other.

7. The adaptor of claim 1, wherein the distal tip of the jet nozzle is positioned within the throat at a position along an axis of the throat.

8. The adaptor of claim 1, wherein the position of the nozzle within the throat is selectively variable between at least two configurations so as to permit the distance from the distal tip of the jet nozzle to the distal end of the tubular wall to be varied by transitioning the position of the nozzle within the throat to one of the at least two configurations.

9. The adaptor of claim 1, wherein the jet nozzle and the tubular wall are provided in separate pieces that are removably connectable to each other.

10. The adaptor of claim 1, wherein the jet nozzle and the tubular wall are provided in a single piece as a unitary construction.

11. An adaptor for fluidly coupling a flow generator to a ventilation mask in a respiratory assistance system, the adaptor comprising:
   a connector which is fluidly connectible to the ventilation mask and defines an interior;
   a tubular wall which protrudes into the interior of the connector and at least partially defines a throat, the tubular wall having a distal end which fluidly communicates with the interior of the connector and a proximal end which is opposite the distal end;
   at least one entrainment port in open fluid communication with ambient air, the at least one entrainment port being at least partially defined by an aperture in the tubular wall between the distal end and the proximal end;
   a jet nozzle in fluid communication with a gas delivery lumen of a main gas delivery tube that is connectable to the flow generator, the jet nozzle having a distal tip that is positioned within the throat at a distance from the distal end of the tubular wall to fluidly communicate gas into the throat with at least a portion of the at least one entrainment port between the distal tip of the jet nozzle and the distal end of the tubular wall, such that when gas is flowed through the gas delivery lumen, out the jet nozzle, and into the throat, ambient air is entrained through the at least one entrainment port; and an exhalation valve, the exhalation valve comprising:
- a housing which is attached to the connector and fluidly communicates with the throat, the housing including at least one exhalation port formed therein; and
- a resilient, conical diaphragm which is disposed within the housing and cooperatively engaged thereto, the diaphragm being selectively movable between open and closed positions relative to the housing; and
- wherein positive pressure and flow in the throat facilitates the stretching of the diaphragm from its open position wherein the exhalation port is unblocked thereby to its closed position wherein it seals against and thus blocks the exhalation port.

12. The adaptor of claim 11, wherein the jet nozzle and the tubular wall are provided in separate pieces that are removably connectable to each other.

13. The adaptor of claim 11, wherein the jet nozzle and the tubular wall are provided in a single piece as a unitary construction.

14. An adaptor for fluidly coupling a flow generator to a ventilation mask in a respiratory assistance system, the adaptor comprising:
- a connector which is fluidly connectible to the ventilation mask and defines an interior;
- a tubular wall which protrudes into the interior of the connector and at least partially defines a throat, the tubular wall having a distal end which fluidly communicates with the interior of the connector and a proximal end which is opposite the distal end;
- at least one entrainment port in open fluid communication with ambient air, the at least one entrainment port being at least partially defined by an aperture in the tubular wall between the distal end and the proximal end;
- a jet nozzle in fluid communication with a gas delivery lumen of a main gas delivery tube that is connectable to the flow generator, the jet nozzle having a distal tip that is positioned within the throat at a distance from the distal end of the tubular wall to fluidly communicate gas into the throat with at least a portion of the at least one entrainment port between the distal tip of the jet nozzle and the distal end of the tubular wall, such that when gas is flowed through the gas delivery lumen, out the jet nozzle, and into the throat, ambient air is entrained through the at least one entrainment port; and
- a piloted exhalation valve, the piloted exhalation valve comprising:
  - a housing which is attached to the connector and defines an interior chamber which fluidly communicates with the throat, the housing including at least one exhaust port formed therein; and
  - a resilient diaphragm which is disposed within the interior chamber and effectively segregates the same into an upper region and a lower region which fluidly communicates with the at least one exhaust port, the diaphragm being selectively movable between an open position wherein the at least one exhaust port is placed into fluid communication with the throat, and a closed position wherein the at least one exhaust port is blocked from fluid communication with the throat.

15. The adaptor of claim 14, wherein the jet nozzle and the tubular wall are provided in separate pieces that are removably connectable to each other.

16. The adaptor of claim 14, wherein the jet nozzle and the tubular wall are provided in a single piece as a unitary construction.

17. The adaptor of claim 14 further comprising a pressure line which facilitates fluid communication between the upper region of the interior chamber and the gas delivery lumen.

18. The adaptor of claim 14 further comprising a biasing spring disposed within the upper region of the interior chamber and extending between the diaphragm and the housing.

19. The adaptor of claim 14 further comprising a resilient flapper valve which is cooperatively engaged to the tubular wall and selectively movable relative thereto between a closed position wherein the flapper valve at least partially obstructs flow into the throat and an open position wherein flow from the throat is substantially unimpeded by the flapper valve.

20. The adaptor of claim 19 wherein the flapper valve includes a plurality of perforations formed therein.

* * * * *